US010386285B2

(12) United States Patent
Petersen et al.

(10) Patent No.: US 10,386,285 B2
(45) Date of Patent: Aug. 20, 2019

(54) INTEGRITY AND FUNCTIONALITY TEST FOR ADSORPTIVE DEPTH FILTER LAYERS WITH AN INORGANIC LAYERED DOUBLE HYDROXIDE

(71) Applicant: Sartorius Stedim Biotech GmbH, Göttingen (DE)

(72) Inventors: Rebecca Petersen, Schifferstadt (DE); Axel Thiefes, Hardegsen (DE); Katrin Köhler, Göttingen (DE); Wolfgang Demmer, Göttingen (DE); Sven Dankenbrink, Ebergötzen (DE)

(73) Assignee: Sartorius Stedim Biotech GMBH, Goettingen (DE)

( * ) Notice: Subject to any disclaimer, the term of this patent is extended or adjusted under 35 U.S.C. 154(b) by 72 days.

(21) Appl. No.: 15/032,220

(22) PCT Filed: Sep. 3, 2014

(86) PCT No.: PCT/EP2014/002384
§ 371 (c)(1),
(2) Date: Apr. 26, 2016

(87) PCT Pub. No.: WO2015/062683
PCT Pub. Date: May 7, 2015

(65) Prior Publication Data
US 2016/0274019 A1    Sep. 22, 2016

(30) Foreign Application Priority Data

Oct. 30, 2013    (DE) .................... 10 2013 018 260

(51) Int. Cl.
*G01N 15/08*        (2006.01)
*G01N 30/88*        (2006.01)
*G01N 30/89*        (2006.01)

(52) U.S. Cl.
CPC .......... *G01N 15/082* (2013.01); *G01N 30/89* (2013.01); *G01N 2015/084* (2013.01); *G01N 2030/889* (2013.01)

(58) Field of Classification Search
CPC .............. G01N 1/4005; G01N 1/405; G01N 2001/4011; G01N 30/96; G01N 30/88; G01N 2015/086; G01N 2030/889; B01D 15/00; B01D 67/0093; B01D 2311/24; B01D 2311/2623; B01D 65/10; B01D 69/02; Y10T 436/16
See application file for complete search history.

(56) References Cited

U.S. PATENT DOCUMENTS

| 6,203,713 | B1 | 3/2001 | Tanny |
| 7,281,410 | B2* | 10/2007 | Phillips ................ B01D 61/00 210/644 |
| 8,696,094 | B2 | 4/2014 | Marcus et al. |
| 2006/0070952 | A1 | 4/2006 | Jin et al. |
| 2011/0207196 | A1 | 8/2011 | Koehler et al. |
| 2012/0264221 | A1 | 10/2012 | Demmer et al. |

FOREIGN PATENT DOCUMENTS

| JP | 3233357 | 11/2001 |
| JP | 3371366 | 1/2003 |

OTHER PUBLICATIONS

Jones, Phil et al. "Determination of arsenate, germanate, phosphate, and silicate by ion chromatography using a post-column reaction (molybdenum blue) detector." Analytica Chimica Acta (1991) 249 539-544 (Year: 1991).*
Kovanda, Frantisek et al. "Removal of anions from solution by calcinated hydrotalcite and regeneration of used sorbent in repeasted calcination-rehydration-anion exchange processes." Collect. Czech. Chem. Commun. (1999) 64 1517-1528. (Year: 1999).*
Cooper, T., The Tools of Biochemistry, pp. 55-56 (1977).
Cavani, F., et al., "Hydrotalcite-Type Anionic Clays: Preparation, Properties and Applications", Catalysis Today, vol. 11, pp. 173-301 (1991).
Yigzaw et al. "Exploitation of the Adsorptive Properties of Depth Filters for Host Cell Protein Removal During Monoclonal Antibody Purification", Biotechnology Progress, American Institute of Chemical Engineers, vol. 22, Jan 1, 2006, pp. 288-296.
Parker et al. "The Use of Hydrotalcite as an Anion Absorbent", Ind. Eng. Chem. Res., vol. 34, 1995, pp. 1196-1202.
Fiske et al., "The Calorimetric Determination of Phosphorus", The Journal of Biological Chemistry, vol. 66, No. 2, Sep. 1925, pp. 375-400.

* cited by examiner

*Primary Examiner* — Christopher Adam Hixson
(74) *Attorney, Agent, or Firm* — McDonnell Boehnen Hulbert & Berghoff LLP

(57) ABSTRACT

The present invention relates to a method for determining the functionality and integrity of depth filter sheets and depth filter sheet systems comprising inorganic layered double hydroxide for contaminant removal in biotechnological processes.

9 Claims, 7 Drawing Sheets

INTEGRITY AND FUNCTIONALITY TEST FOR ADSORPTIVE DEPTH FILTER LAYERS WITH AN INORGANIC LAYERED DOUBLE HYDROXIDE

FIELD OF THE INVENTION

The present invention relates to a method for determining the functionality and integrity of depth filter sheets and depth filter sheet systems comprising inorganic layered double hydroxide for contaminant removal in biotechnological processes.

BACKGROUND OF THE INVENTION

The definitions described hereinbelow underlie the present invention. "Adsorptive material separation" is understood to mean the removal of one or more components from a fluid phase by selective adsorption of said component(s) to a solid phase, the "adsorbent" (plural "adsorbents"). The field of the invention generally relates to material separation in liquids, liquid being referred to hereinafter as "medium". Adsorbents are porous solids which can selectively form bonds with certain components of fluids via functional surface groups referred to as "ligands". In addition to the "particulate adsorbents", also referred to as chromatography gels, which have been known for a long time, further "nonparticulate adsorbents" based on a completely different matrix have become established. These are so-called monolithic adsorbents composed of a three-dimensional porous solid body or support based on microporous membranes composed of various polymers. Adsorption membranes refer to planar adsorbents having pores passing through from one side to the other.

According to the invention, target substance(s) and/or contaminant(s) are referred to as "adsorbate" and used in the singular, though two or more different substances may also be involved. The "capacity" of an adsorbent is understood to be a quantitative measure of its uptake capacity for adsorbate. The capacity is based on a defined amount of adsorbent.

The present invention relates to the technical field of depth filter sheets and depth filter sheet systems comprising inorganic layered double hydroxides, as described in DE 10 2008 037 678 A1 for example, which are used for contaminant removal in biotechnological processes. In this connection, said depth filter sheets and depth filter sheet systems comprising inorganic layered double hydroxides are used to remove undesired biological components, such as, for example, nucleic acids, cellular proteins, viruses or endotoxins, from process solutions as filtration medium, the undesired biological components being adsorptively bound to the depth filter, and the desired target products, such as, for example, antibodies, hormones, enzymes, (poly)peptides and, more particularly, therapeutic proteins, however, being able to pass through the depth filter unimpeded.

Nucleic acids are to be understood here to mean all naturally occurring nucleic acids such as ribonucleic acid (RNA) and deoxyribonucleic acid (DNA), more particularly DNA of genomic or else epigenomic origin from eukaryotic, prokaryotic and viral sources, and very particularly nucleic acids having a chain length of more than 15 base pairs.

Said depth filter sheets and depth filter sheet systems comprising inorganic layered double hydroxides have a high capacity for depleting DNA and other contaminants and have, at the same time, a low amount of extractable constituents from the filter material, and so they are suitable for use before and after the chromatographic process step in downstream processes. The breakthrough of contaminants is a critical factor in validated biopharmaceutical processes. The use of depth filters and depth filter systems for contaminant removal requires a way of checking the quality of the filter and of being able to make a prediction about the binding capacity and the integrity of the depth filters and depth filter systems.

Because of the new types of properties of depth filter sheets and depth filter sheet systems and because of the associated new fields of use for contaminant removal in downstream processes, it is necessary to test the depth filter sheets and depth filter systems comprising inorganic layered double hydroxide before their use with respect to their integrity and functionality. The further development of depth filter sheets for critical applications also requires the further development of ways of testing said new properties.

To date, conventional depth filters and depth filter systems are used in biopharmaceutical processes to remove particles, especially in the clean-up of cell culture solutions to remove cells and cellular constituents. In this connection, a qualification of the filters is done by checking the filter thicknesses and water flow rates. An additional integrity check is not necessary for these noncritical applications.

JP 3233357 B2 discloses an integrity test for depth filters, in which said filter is subjected to a diffusion test at 0.2 bar. Using said integrity test, it is possible to establish only very large defects above a "bubble point" value of 0.2 bar. In the integrity test known from JP 3233357 B2, there is also no correlation between the result of the integrity test and the binding capacity of the depth filter for biomolecules.

JP 3371366 B2 discloses an integrity test method similar to that of the aforementioned document, in which depth filters wetted with water are subjected to a gas permeability test near the "bubble point" value.

For contaminant removal, use is also made of nonparticulate adsorbers, such as, for example, the membrane adsorber Sartobind® Q from Sartorius Stedim Biotech GmbH. For the qualification of said nonparticulate adsorbers, the applicant discloses in DE 10 2010 004 188 A1 a method in which the nonparticulate ion-exchanger adsorber a) has alkaline solution applied thereto in the case of an anion exchanger or has acid applied thereto in the case of a cation exchanger, b) is rinsed with water, c) has a liquid ion-containing medium applied thereto with detection of the concentration of the broken-through ions by means of an ion-sensitive probe and d) the concentration profile detected in c) is compared with that of a nonparticulate ion-exchanger adsorber of known integrity.

In DE 10 2010 004 190 A1, the applicant discloses a further method, in which a nonparticulate adsorber (membrane adsorber) loaded with an adsorbate under conditions under which the adsorbate is retained by the nonparticulate adsorber (membrane adsorber), the breakthrough of the adsorbate, for example of phosphate ions, is detected with very high accuracy by means of a secondary reaction, and the breakthrough characteristics of the phosphate ions is compared with those of a nonparticulate adsorber of known integrity.

The basis of the two methods disclosed by the applicant is that, during the application of a liquid, ion-containing medium to the membrane adsorber, these ions are completely retained until the breakthrough volume is reached and the excess ions in the filtrate are appropriately detected only after the breakthrough volume is reached. In this connection, the binding of the ions to the matrix of the membrane adsorber is done to the porous structure. The basis is a microfiltration membrane comprising its multiplicity of pores having a relatively narrow pore size distribution with a minimum and a maximum pore size. Functional groups are chemically bonded to the surface of said pores. As a result of the interaction with said functional groups, the adsorbates are adsorptively bound when flowing through the membrane.

These methods disclosed by the applicant are generally not suitable for depth filter sheets and depth filter sheet systems, since a breakthrough of the liquid ion-containing medium takes place immediately, and this is to be expected in view of the typical structure of a depth filter. Depth filter sheets have a structure completely different to that of membrane adsorbers. They consist of a sheet of cellulose fibers lying on top of one another in an irregular manner and pulverulent adsorbents bound to the cellulose fibers by means of a binder. Depth filters have a broad pore distribution without the exclusion of a minimum and a maximum pore size. As a result, depth filters generally do not have an absolute separation limit. For a depth filter, the pore shape and distribution is irregular and not clearly defined owing to the fiber structure. Therefore, in a depth filter, the density and distribution of the adsorbing particles and also their binding sites are more irregular than in the case of a membrane adsorber.

When ion-containing media are applied to a depth filter, these ions are generally depleted, but not completely retained. For instance, the application of ions according to DE 10 2010 004 188 A1 or DE 10 2010 004 190 A1 to conventional, commercially available depth filter sheets and depth filter sheet systems containing kieselguhr as pulverulent adsorbents, such as, for example, S9P from Sartorius Stedim Biotech GmbH or Beco Steril S100 from Begerow, shows in said application an immediate breakthrough of the described ions and adsorbates. Consequently, these integrity test methods described by the applicant for the qualification of nonparticulate adsorbents are not suitable for determining the integrity and functionality of depth filter sheets and depth filter sheet systems, i.e. checking the quality, more particularly the integrity, of the filter and making a prediction about binding capacity.

SUMMARY OF THE INVENTION

It is an object of the present invention to provide a qualification method for adsorptive depth filter sheets and depth filter sheet systems comprising inorganic layered double hydroxide, which method allows a highly sensitive, robust, simple, nondestructive testing of filters and filter elements with respect to their integrity and functionality. For the qualification, preference is to be given to using aids which do not signify impairment of the function of the depth filter or of product quality.

This object is achieved by providing a method for determining the integrity and functionality of adsorptive depth filter sheets and depth filter sheet systems comprising inorganic layered double hydroxide as claimed in claim 1.

More particularly, the present invention provides a method which makes it possible to test the functionality and the integrity of depth filter sheets and depth filter sheet systems comprising inorganic layered double hydroxide in their use to retain contaminants, such as, for example, nucleic acids, cellular proteins, viruses or endotoxins.

According to the present invention, the method for determining the integrity and functionality of depth filter sheets and depth filter sheet systems comprising inorganic layered double hydroxides comprises the steps of loading the depth filter sheet comprising inorganic layered double hydroxide with an adsorbate, comprising inorganic anions, under conditions under which the adsorbate is completely retained by the adsorptive depth filter sheet until the breakthrough volume is reached, detecting the broken-through adsorbate by means of a secondary reaction, the negative common logarithm of the detected limit concentration pD being ≥4, and comparing the breakthrough characteristics with those of an adsorptive depth filter sheet of known integrity.

According to the invention, "under conditions under which the adsorbate is completely retained by the adsorptive depth filter sheet until the breakthrough volume is reached" is understood to mean conditions under which the depth filter sheet is pretreated with a phosphate-free buffer solution within the pH range of 5 to 14.

According to the invention, said method makes it possible to detect with very high precision and sensitivity imperfections and defects in depth filter sheets and depth filter sheet systems comprising inorganic layered double hydroxide. Associated therewith, said method advantageously makes it possible to test the retention capacity for contaminants, such as, for example, viruses, nucleic acids, cellular proteins and endotoxins.

The sensitivity of an analytical detection can be described by the limit concentration or the pD value. The term limit concentration refers to that concentration in g/ml of a substance to be detected, at which the detection is still positive. For simplicity, the pD value, which is defined as the negative common logarithm of the limit concentration, is implemented instead of the limit concentration.

According to the present invention, the negative common logarithm of the detected limit concentration is pD≥4, preferably pD≥5, more preferably pD≥6.

According to the invention, any secondary reaction by means of which a corresponding sensitivity of detection for the broken-through adsorbate or parts thereof can be raised to the above-described detectable limit concentration is suitable. Examples thereof are complex formations with a precipitation reaction or with a color reaction, with preference being given to a color reaction.

According to the present invention, it has been found that, surprisingly and advantageously, when applying inorganic anions to an intact depth filter sheet and to a depth filter sheet system, comprising in each case an inorganic layered double hydroxide, said anions are initially completely adsorbed and retained by the depth filter sheets and depth filter sheet systems comprising inorganic layered double hydroxides until the breakthrough volume is reached, contrary to the above-described expectation that an immediate breakthrough of the medium containing the ions should take place. In the event of damage and/or an error in the manufacture of an adsorptive depth filter sheet, the breakthrough and its characteristics are shifted in such a way that said breakthrough takes place earlier, since the retention capacity of the depth filter sheet is impaired and thus more adsorbate can break through in comparison with an intact adsorptive depth filter sheet.

Since, in the presence of a defect in the depth filter sheet system comprising inorganic layered double hydroxide, the breakthrough of the adsorbate takes place prematurely and distinctly differs from the breakthrough of an intact depth filter sheet system comprising inorganic layered double hydroxide, it is advantageously possible to make a prediction about the integrity of the depth filter. Surprisingly and advantageously, it is possible according to the present invention for said integrity to be detected even in the case of only slight impairment of the adsorptive depth filter sheet because of the sensitivity of the method.

According to a preferred embodiment of the present invention, the inorganic anions encompass phosphate ions selected from the group of the oxygen acids of phosphorus. In this connection, the depth filter sheet is loaded with the phosphate ions preferably in the form of their water-soluble metal salts. In the preferred case of the depth filter sheets and depth filter sheet systems comprising inorganic layered double hydroxide being loaded with phosphate ions, the detection of the phosphate ions in the filtrate can be achieved preferably in the form of a phosphomolybdenum blue complex, as described in C. H. Fiske et al., J. Biol. Chem. 66, (1925) 375-400. In this connection, within the scope of the method according to the invention, it is surprising that, despite the high analytical sensitivity of said detection, phosphate is not detected in the filtrate in the case of intact depth filter sheets comprising inorganic layered double hydroxide before the breakthrough is reached.

The detection of phosphate as phosphomolybdenum blue, as described in this invention, has a limit concentration of 1 nmol/ml or $1.36 \times 10^{-7}$ g/ml for potassium dihydrogen phosphate ($KH_2PO_4$) with the molar mass of 136.09 g/mol and corresponds to a pD of 6.9. This means that the sensitivity of said detection is higher by two or more orders of magnitude with respect to the majority of known methods.

In the method according to the invention, the depth filter sheets and depth filter sheet systems comprising inorganic layered double hydroxide are preferably subjected to the flow-through of phosphate ions within a concentration range of 0.5 mmol/l to 50 mmol/l and the concentration thereof in the collected filtrate is determined as described above. According to a preferred embodiment of the present invention, the ion concentration in the adsorbate is 1.0 mmol/l or more, and particularly preferably 1.5 mmol/l or more. The upper limit of the ion concentration in the adsorbate is preferably 40 mmol/l, more preferably 30 mmol/l and particularly preferably 20 mmol/l.

As will be described later on in more detail, the breakthrough volume is determined irrespective of the integrity of the depth filter sheet comprising inorganic layered double hydroxide to be tested, of the ion concentration of the adsorbate, and of the adsorption capacity of the depth filter sheet, which correlates with the concentration of inorganic layered double hydroxide. To ensure a reliable determination of the integrity and functionality of depth filter sheets and depth filter sheet systems comprising inorganic layered double hydroxide, the above factors should be selected in such a way that the breakthrough volume is sufficiently large in the case of intact depth filter sheets, so as to be able to make a precise statement about defects and imperfections. This means that, in the case of depth filter sheets comprising a relatively small proportion of inorganic layered double hydroxide, the ion concentration of the adsorbate should be accordingly lower and, in the case of depth filter sheets comprising a relatively large proportion of inorganic layered double hydroxide, the ion concentration of the adsorbate can be selected accordingly higher.

The method according to the invention can be used for all known depth filter sheets and depth filter sheet systems comprising inorganic layered double hydroxides. Preferably, these are depth filter sheet systems comprising inorganic layered double hydroxide having a cationic sheet structure and exchangeable anions in the intermediate sheets, as described in DE 10 2008 037 678 A1 and in "Catalysis Today" 1991, 11(2), pages 173-201, more particularly page 176 to page 191, but without being restricted thereto. This means that the present invention can be applied to all adsorptive depth filter sheets and depth filter sheet systems which comprise an inorganic layered double hydroxide, more particularly hydrotalcite.

As the concentration or proportion by weight of the inorganic layered double hydroxide in the adsorptive depth filter sheet increases, the position of the ion breakthrough shifts toward larger filtrate volumes owing to differing adsorption capacity. This is advantageous for a reliable determination of the integrity and functionality of depth filter sheets, since it is possible to make in this regard a more precise statement as to, for example, whether there is a defect in the depth filter sheet. According to a preferred embodiment of the present invention, the proportion by weight of the inorganic layered double hydroxide in the adsorptive depth filter sheet is 20% or more, more preferably 30% or more, particularly preferably 35% or more and most preferably 39% or more. Preferred upper limits for the proportion by weight of the inorganic layered double hydroxide are 80%, more particularly 70%.

According to a preferred embodiment of the method according to the invention, the inorganic layered double hydroxide comprises hydrotalcite.

According to one embodiment of the present invention, the depth filter sheets and depth filter sheet systems comprise, in addition to the cellulose fibers and the inorganic layered double hydroxide, preferably kieselguhr as pulverulent adsorbent. In this case, particular preference is given to a mixture of hydrotalcite and kieselguhr, in which the proportion by weight of hydrotalcite is greater than that of kieselguhr, more particularly at least double.

However, according to a preferred embodiment, the depth filter sheets and depth filter sheet systems comprise, in addition to the cellulose fibers and the inorganic layered double hydroxide, no further pulverulent adsorbent.

It is advantageous in the method according to the invention to use only aids which, when used, do not impair the functionality of the depth filter sheets and depth filter sheet systems comprising inorganic layered double hydroxide in the majority of biotechnological applications. As a result, it is possible according to a preferred embodiment of the present invention for the loading with an adsorbate to be reversible. Consequently, the method according to the invention can preferably be used as a so-called "pre-use test" prior to the use of the depth filter sheets and depth filter sheet systems comprising inorganic layered double hydroxide. This ensures that the adsorptive depth filter sheet can be used after qualification in relation to the relevant use thereof without loss of performance. If the depth filter sheets have already been used as intended to remove contaminants, such as DNA for example, and said contaminants can be removed from the depth filter sheets without leaving residue, the method according to the invention can also be carried out as a so-called "post-use test" after the relevant adsorptive material separation.

As described above, the application of inorganic ions to the adsorptive depth filter sheet during the method according to the invention leads to a loading of the depth filter sheet with said inorganic ions, which can be removed by means of a treatment with, for example, carbonate-containing rinse solution (reload), and so the depth filter sheet regains its original binding capacity for a subsequent intended use to an extent of at least 90% and, according to a preferred embodiment of the reload, to an extent of at least 95%.

Furthermore, the method according to the invention is notable for the fact that the breakthrough of the inorganic ions correlates with the retention capacity with respect to biomolecules, such as, for example, BSA (bovine serum albumin), DNA or IVIG (intravenous immunoglobulin). Preferably, said biomolecules are biomolecules selected from the group of serum albumins, nucleic acids and immunoglobulins or combinations thereof. As a result, it is advantageously possible to make a prediction about the binding capacity with respect to said biomolecules. Since there is a linear correlation between the phosphate breakthrough and the binding capacity for biomolecules, for example BSA, IVIG and DNA, it is possible, after the determination of a standard curve based on the experimentally determined values for the phosphate breakthrough, to predict with high precision the expected binding capacity for the aforementioned biomolecules.

DESCRIPTION OF THE DRAWINGS

The present invention will now be more particularly elucidated by means of the following exemplary embodiments and FIGS. 1 to 7, where.

DESCRIPTION OF THE INVENTION

Filter Materials

Figure 1:
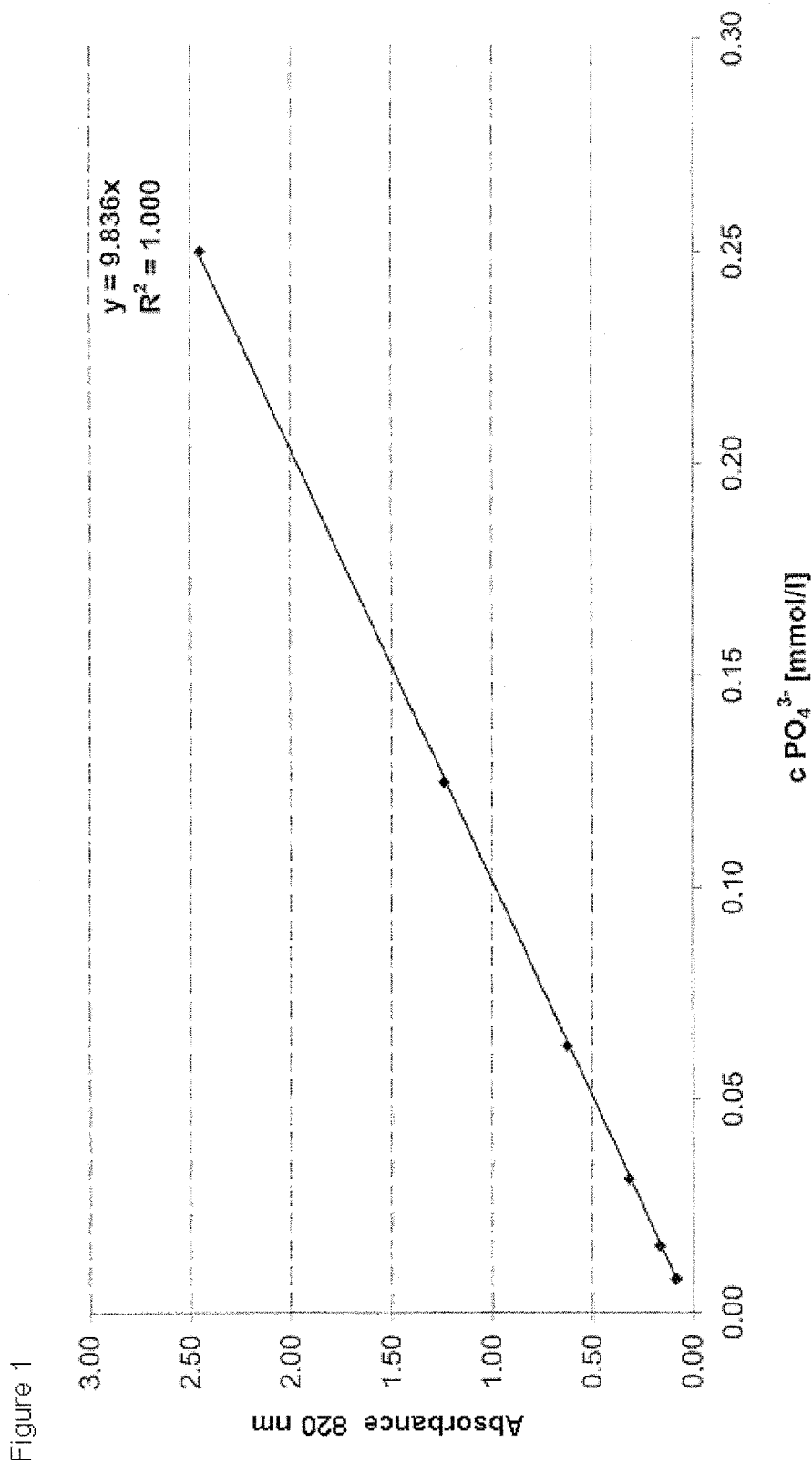
FIG. 1 shows a standard curve in relation to the photometric determination of the concentration of phosphate as phosphomolybdenum blue at 820 nm using a Tecan photometer.

The adsorptive depth filter sheets comprising inorganic layered double hydroxide that were used were produced according to DE 10 2008 037 678 A1. They differ in the composition of the recipe, i.e., in the type of hydrotalcite, cellulose and/or kieselguhr, the hydrotalcite content, the cellulose content, and the kieselguhr content. Table 1 shows an overview of the composition of the adsorptive depth filter sheets comprising inorganic layered double hydroxide that were used. Hydrotalcite type A has a magnesium oxide/aluminum oxide ratio of 1.65 and is not calcined. Hydrotalcite type B has a magnesium oxide/aluminum oxide ratio of 1.72 and is calcined. Hydrotalcite type C is chemically identical to type A and differs from type A in the particle size. Hydrotalcite type A has a d(1.0) value of 25 μm and type C has a d(1.0) value of 280 μm. The d(1.0) value is the value in μm in which 100% of the particles of a sample are smaller than the specified d(1.0) value. The d(1.0) value therefore indicates the maximum size ranges for the largest particles of a sample.

The comparative examples used were the conventional, commercially available depth filter sheets S9P from Sartorius Stedim Biotech GmbH and Beco Steril S100 from Begerow, which contain kieselguhr as pulverulent adsorbents and differ, as shown in Table 1, in the type and concentration of cellulose and kieselguhr.

TABLE 1

Overview of components and compositions of the adsorptive depth filter sheets used.

| Filter | Hydro-talcite (HT) | Recipe HT [%] | Recipe Cellulose [%] | Recipe Kieselguhr [%] |
|---|---|---|---|---|
| No. 1 comprising 39% HT type A | Type A | 39 | 39 | 22 |
| No. 2 comprising 46% HT type A | Type A | 46 | 34 | 20 |
| No. 3 comprising 64% HT type A | Type A | 64 | 36 | 0 |
| No. 4 comprising 64% HT type C | Type C | 64 | 36 | 0 |
| No. 5 comprising 58% HT type B | Type B | 58 | 42 | 0 |
| No. 6 comprising 50.9% HT type B | Type B | 50.9 | 49.1 | 0 |
| No. 7 comprising 46.2% HT type B | Type B | 46.2 | 53.8 | 0 |
| Sartorius S9P | — | 0 | 52.5 | 47.5 |
| Begerow Beco Steril S100 | — | 0 | 42 | 58 |

Example 1 —Determination of the Standard Curve for the Determination of Phosphate as Phosphomolybdenum Blue The following reagents were prepared:
1.1 TBS Buffer
10 mmol TBS buffer (TRIS-buffered saline solution), pH 7.4, composed of 1.21 g of tris(hydroxymethyl)aminomethane (TRIS), 8.8 g of NaCl with reverse osmosis water (RO water) made up to 1 liter, adjusted to pH 7.4 using HCl.
1.2 Phosphate Solution
1 mmol $PO_4^{3-}$ solution in 10 mmol TBS composed of 0.178 g of $Na_2HPO_4 \cdot 2H_2O$ in 1000 ml of TBS buffer (from 1.1).
1.3 Detection Reagent
Reagent A: 5 g of ascorbic acid is dissolved in 50 ml of water.
Reagent B: 6 N sulfuric acid (12 ml of a 98% strength sulfuric acid are added to 60 ml of water).
Reagent C: 1.25 g of ammonium heptamolybdate are dissolved in 50 ml of water.
50 ml of each of reagents A, B and C are thoroughly mixed with 100 ml of RO water. This working solution is freshly prepared prior to each determination series.

To obtain a concentration series, the phosphate solution according to 1.2 was diluted with TBS buffer from 1.1 in accordance with Table 2 to give a standard solution of various phosphate concentrations. Thereafter, 1 ml of working solution was added to 1 ml in each case of said standard solution and thoroughly mixed. The preparations were placed in a 70° C. water bath for 10 min. The preparations were then measured in a suitable glass cuvette in a spectrophotometer at 820 nm against a reagent blank (1 ml of water+1 ml of working solution).

A typical standard curve is shown in Table 2 and FIG. 1.

TABLE 2

Values of the standard curve for the determination of phosphate as phosphomolybdenum blue by means of UV absorbance

| Phosphate in mmol/l | Absorbance at 820 nm |
| --- | --- |
| 0.00781 | 0.0818 |
| 0.01563 | 0.1592 |
| 0.03125 | 0.3148 |
| 0.06250 | 0.6257 |
| 0.12500 | 1.2403 |
| 0.25000 | 2.4496 |

It is apparent that there is a linear dependency of the UV absorbance in relation to the amount of phosphate used. The coefficient of determination for the curve is $R^2=1.000$. The phosphate ions are captured here as a blue phosphomolybdenum blue complex as per T. G. Cooper, "The Tools of Biochemistry", John Wiley & Sons, 1977, pages 55-56, and C. H. Fiske and Y. P. Subbarow, J. Biol. Chem. 66, (1925), 375-400.

Example 2 — Breakthrough Curve on a Depth Filter Sheet Comprising Inorganic Layered Double Hydroxide During the Application of Phosphate Ions The depth filter sheet comprising inorganic layered double hydroxide No. 4, produced according to DE 10 2008 037 678 A1, having the composition shown in Table 1 was clamped in a suitable device and used as follows:
1. Rinsing of the adsorptive depth filter sheet system comprising inorganic layered double hydroxide (13.2 cm$^2$) with 100 ml of a TRIS buffer solution (10 mmol, pH 7.4) at a flow rate of 5 ml/min.
2. Application of phosphate solution (5 mmol KH$_2$PO$_4$ solution in 10 mmol TRIS, pH 7.4) to the adsorptive depth filter sheet system comprising inorganic layered double hydroxide at a flow rate of 4 ml/min.
3. Collection of the filtrate in 1 ml fractions.
4. Determination of the phosphate concentrations in the individual fractions as per Example 1. The concentration $c_i$ of fraction i is calculated from the absorbance $E_i$ and the gradient m of the standard curve according to $$c_i = E_i/m. \quad (1)$$

5. Plotting of the phosphate concentration in the filtrate against the filtrate volume on a graph in the form of a breakthrough curve.
6. Determination of the breakthrough value $V_D$.
   $V_D$ is the filtrate volume at which a phosphate concentration having an absorbance $A_{820\ nm}=0.03$ can be detected for the first time (corresponds to 1% of the absorbance that is maximally detectable here). It is determined from the two fractions, the absorbance of which is just below or just above the value of 0.03. Between these two pairs of values $x_1/y_1$ and $x_2/y_2$, linear interpolation is carried out and the x value for y=0.03 is determined. The following apply:

$$V_D = x_1 + (0.03 - y_1) \cdot \left(\frac{x_2 - x_1}{y_2 - y_1}\right) \text{ or } V_D = x_2 + (0.03 - y_2) \cdot \left(\frac{x_2 - x_1}{y_2 - y_1}\right) \quad (2)$$

7. Determination of the loading number $L_{phosphate}$ for phosphate.
   The loading number $L_{Phosphate}$ in mg/cm$^3$ is calculated according to $$L_{Phosphate}[\text{mg/cm}^3] = \frac{c_{Phosphate}[\text{mol/l}] \cdot V_D[\text{ml}] \cdot M_{Phosphate}[\text{g/mol}]}{t[\text{cm}] \cdot \pi \cdot r[\text{cm}]^2} \quad (3)$$

where the following apply:
radius of the punch-out r=2.35 cm
average molar mass of phosphate at pH=7.4 $M_{phosphate}$=96.37 g/mol
concentration of phosphate in the test solution $C_{Phosphate}$=0.001 mol/l
filter thickness t in cm
breakthrough $V_D$ in ml determined according to 6.

Figure 2:
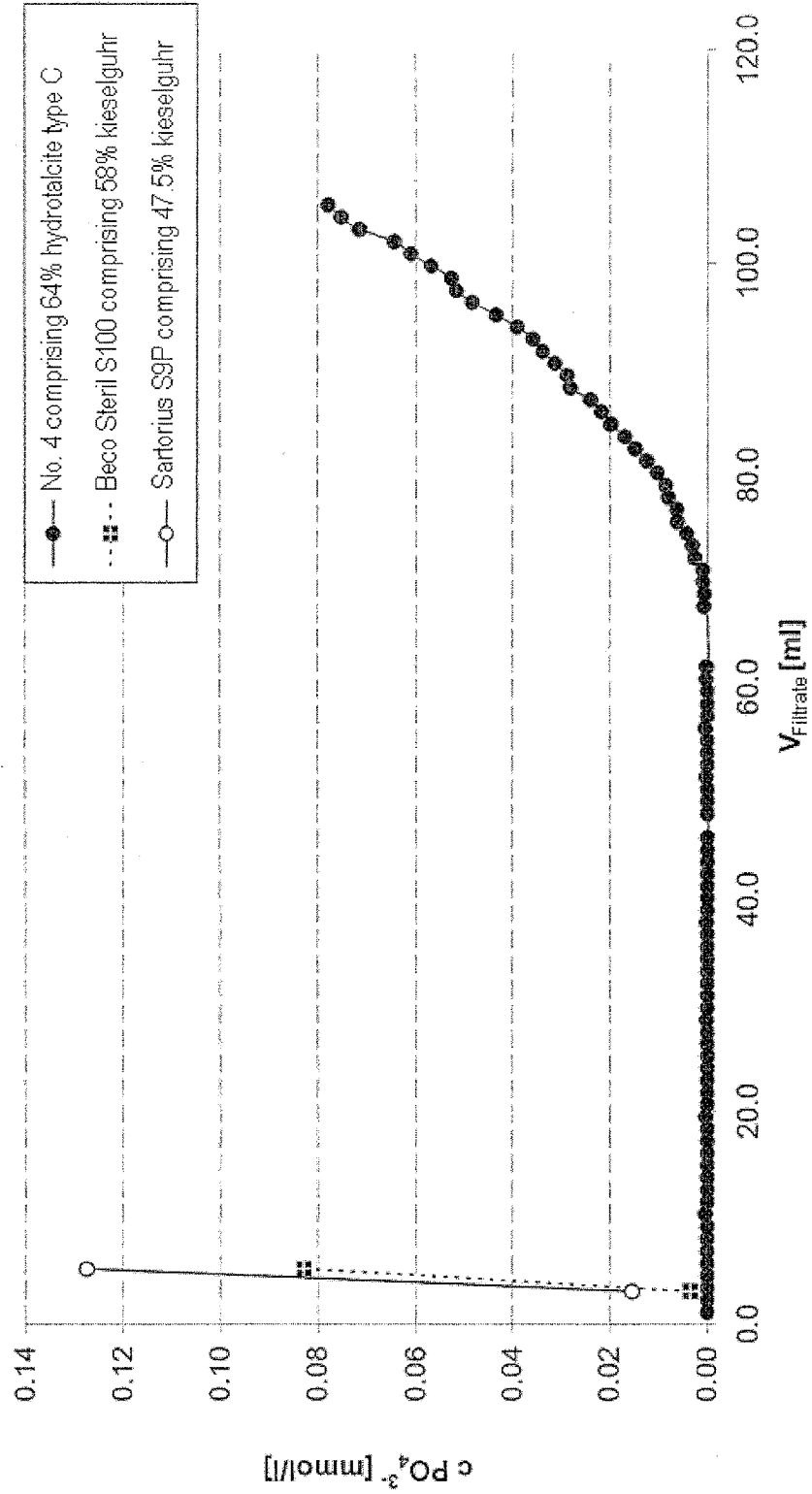
FIG. 2 shows the phosphate breakthrough curves on the adsorptive depth filter sheet system comprising inorganic layered double hydroxide No. 4 during the application of phosphate ions at a concentration of 1 mmol/l as per Example 2 in comparison with conventional, commercially available depth filter sheets comprising kieselguhr.

FIG. 2 shows the profile of the phosphate concentration in the outflow during the application of KH$_2$PO$_4$ solution in the inflow to the adsorptive depth filter sheet system containing inorganic layered double hydroxide. The concentration of the phosphate ions in the outflow during the application to the adsorptive depth filter sheet system comprising inorganic layered double hydroxide is initially zero before then sharply rising when saturation of the adsorptive depth filter sheet system comprising inorganic layered double hydroxide is reached. The position of the phosphate breakthrough on the x-axis can be detected very accurately on the basis of the emerging phosphate ions in the outflow. By comparison, FIG. 2 shows the profiles of the phosphate concentration in the outflow during the application of KH$_2$PO$_4$ solution in the inflow to conventional, commercial adsorptive depth filter sheets S9P from Sartorius Stedim Biotech GmbH and Beco Steril S100 from Begerow, which both contain kieselguhr. The breakthrough of the phosphate ions takes place immediately for the non-hydrotalcite-containing depth filter sheets of the comparative examples.

Therefore, the depth filter sheets of the comparative examples cannot have their integrity tested using the method according to the invention, whereas depth filter sheets comprising inorganic layered double hydroxide can have their integrity tested in a reproducible and reliable manner using the method according to the invention.

Figure 3:
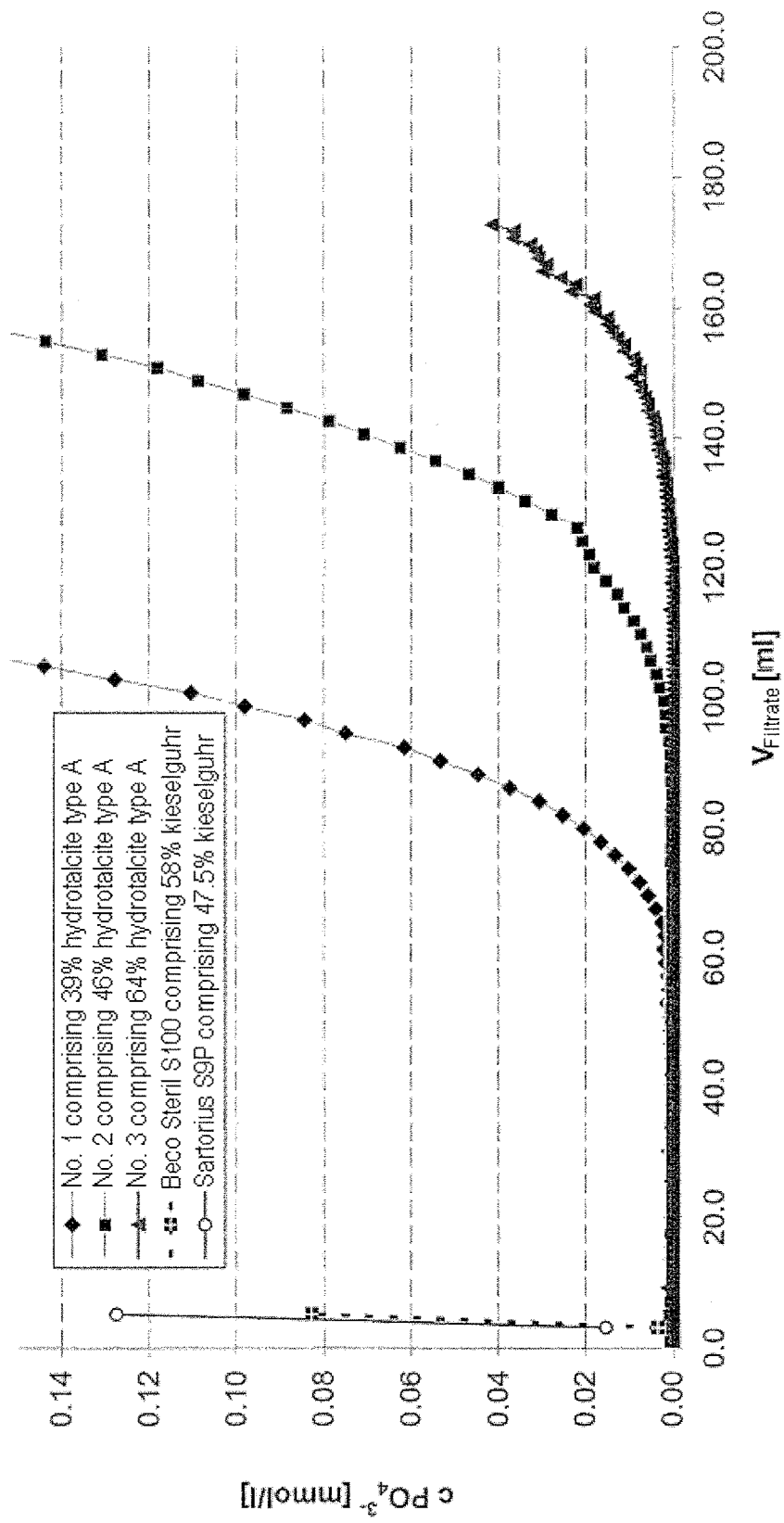
FIG. 3 shows the phosphate breakthrough curves on depth filter sheet systems comprising various concentrations of inorganic layered double hydroxide (No. 1 to No. 3) during the application of phosphate ions as per Example 2 in comparison with conventional, commercially available depth filter sheets comprising kieselguhr.

Example 3 — Breakthrough Curves on Adsorptive Depth Filter Sheet Systems Comprising Various Concentrations of Inorganic Layered Double Hydroxide During the Application of Phosphate Ions Adsorptive depth filter sheet systems comprising various concentrations of inorganic layered double hydroxide were used. The procedure was as per Example 2. KH$_2$PO$_4$ solution was applied as per the procedure in Example 2. FIG. 3 shows the breakthrough curves for adsorptive depth filter sheet systems comprising various concentrations of inorganic layered double hydroxide. It is clearly evident that the position of the phosphate breakthrough shifts toward greater filtrate volumes as the concentration of hydrotalcite increases as a result of their differing adsorption capacity. It is further evident that a content of, for example, 39% hydrotalcite allows the testability of the depth filter, compared to the comparative-example filters which contain only kieselguhr and for which integrity is not testable.

Example 4 —Breakthrough Curve on an Adsorptive Depth Filter Sheet System Comprising Inorganic Layered Double Hydroxide During the Application of Phosphate Ions of Different Concentrations in the Inflow The depth filter sheet comprising inorganic layered double hydroxide No. 4, produced according to DE 10 2008 037 678 A1, having the composition shown in Table 1 was used.

Figure 4:
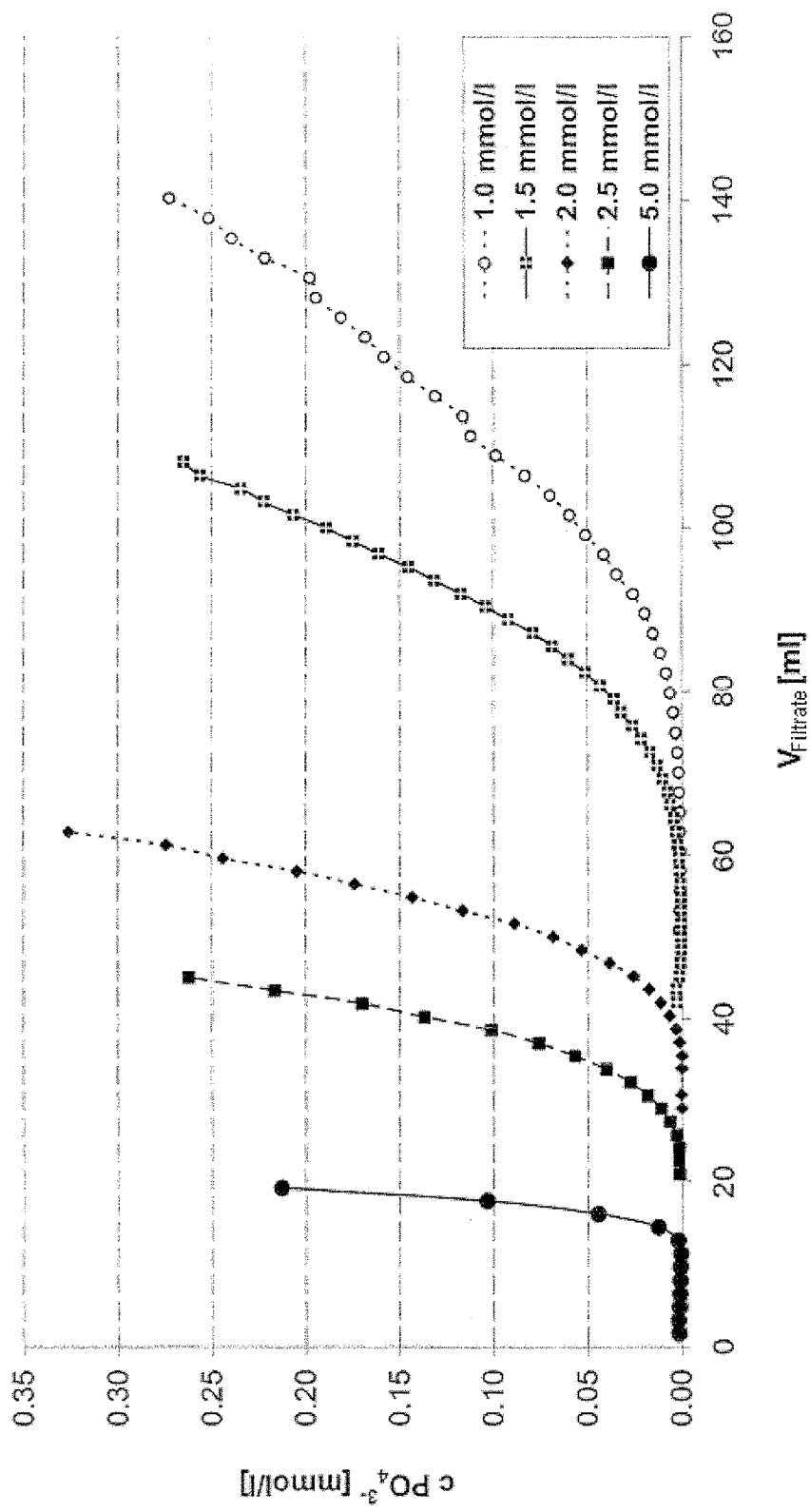
FIG. 4 shows the phosphate breakthrough curves on the adsorptive depth filter sheet system comprising inorganic layered double hydroxide No. 4 during the application of phosphate ions as per Example 2 for various phosphate concentrations in the inflow.

The procedure was as per Example 2. $KH_2PO_4$ solution of various concentrations was applied, and the outflow was collected in a fractionated manner in 1 ml volume units. The phosphate concentration was determined as in Example 1 and plotted against the filtrate volume. The breakthrough curves are shown in FIG. 4.

Example 5 —Breakthrough Curves on Various Compositions of Adsorptive Depth Filter Sheet Systems Comprising Inorganic Layered Double Hydroxide During the Application of Phosphate Ions Various variants of adsorptive depth filter sheet systems comprising inorganic layered double hydroxide were used, differing in the components and their composition as per Table 1.

Figure 5:
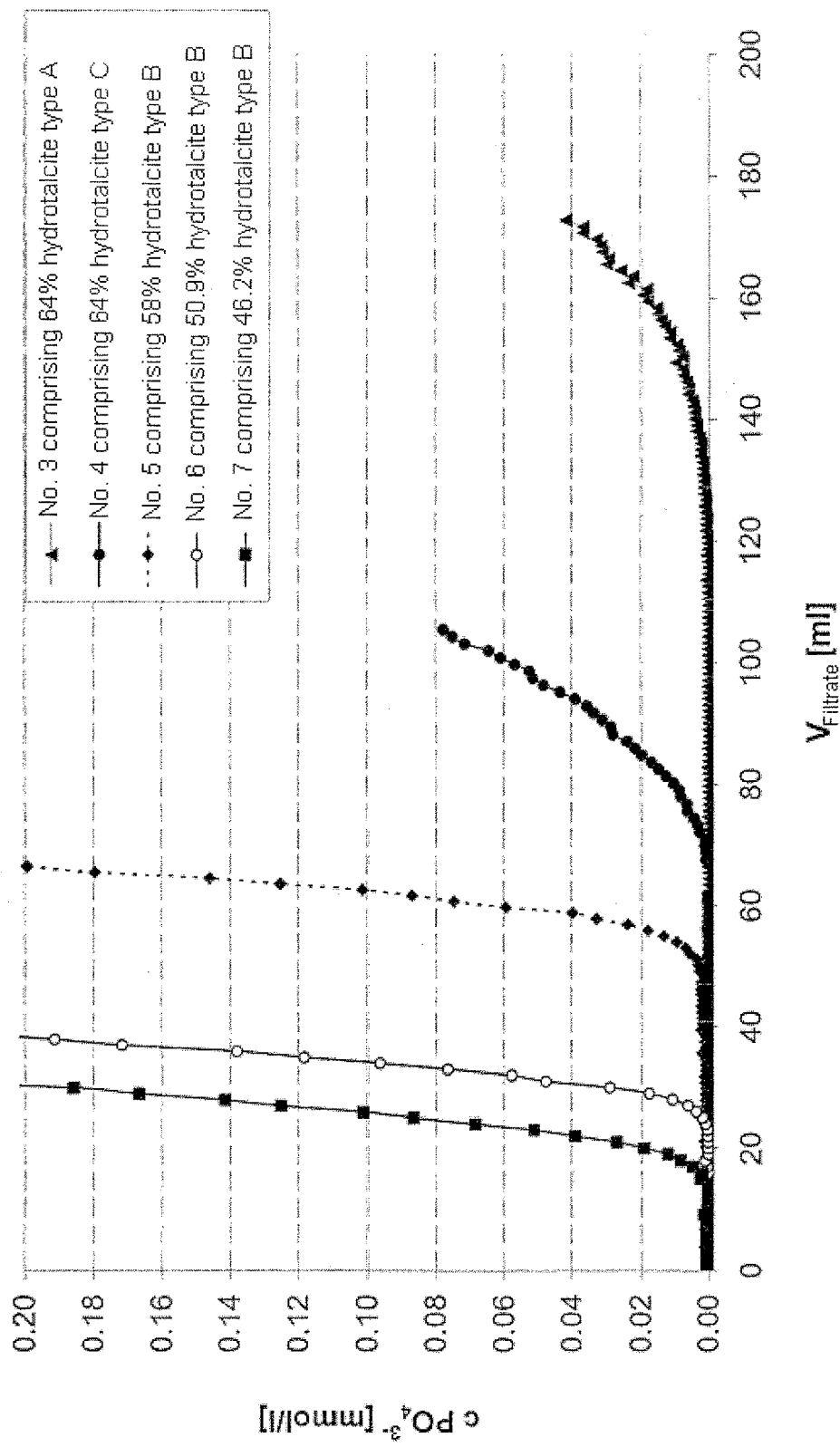
FIG. 5 shows the phosphate breakthrough curves for adsorptive depth filter sheet systems comprising various compositions of inorganic layered double hydroxide (No. 3 to No. 7) during the application of phosphate ions at a concentration of 1 mmol/l as per Example 2.

The procedure was as per Example 2. $KH_2PO_4$ solution was applied as per the procedure in Example 2. FIG. 5 shows the breakthrough curves for various compositions of adsorptive depth filter sheet systems comprising inorganic layered double hydroxide. The depth filter sheet systems differ in the type and composition of the hydrotalcite and of the cellulose and are characterized by the position of their phosphate breakthrough as a result of their differing adsorption capacity.

Example 6 —Dynamic Protein Binding

To determine the dynamic binding capacities of the depth filter sheets, punch-outs having the diameter of 47 mm and an effective filter area of 13.2 cm$^2$ are wetted with 10 ml of RO water, inserted into a stainless steel filtration housing (from Sartorius Stedim Biotech GmbH) and prerinsed with 100 ml of TBS (as per Example 1) at 4 ml/min and then rinsed through with a protein or DNA test solution. The test solutions used are a) a freshly prepared solution of BSA (bovine serum albumin from Roth) of a concentration of 1 g/l in TBS buffer (as per Example 1)
b) a solution of salmon sperm DNA (Na salt, size distribution 500-1000 base pairs, product number 54653 from Biomol) of a concentration of 0.5 mg/ml and
c) a solution of intravenous immunoglobulin IVIG of a concentration of 1 g/l (Cytoglobin® from Bayer Vital, Leverkusen).

Figure 6:
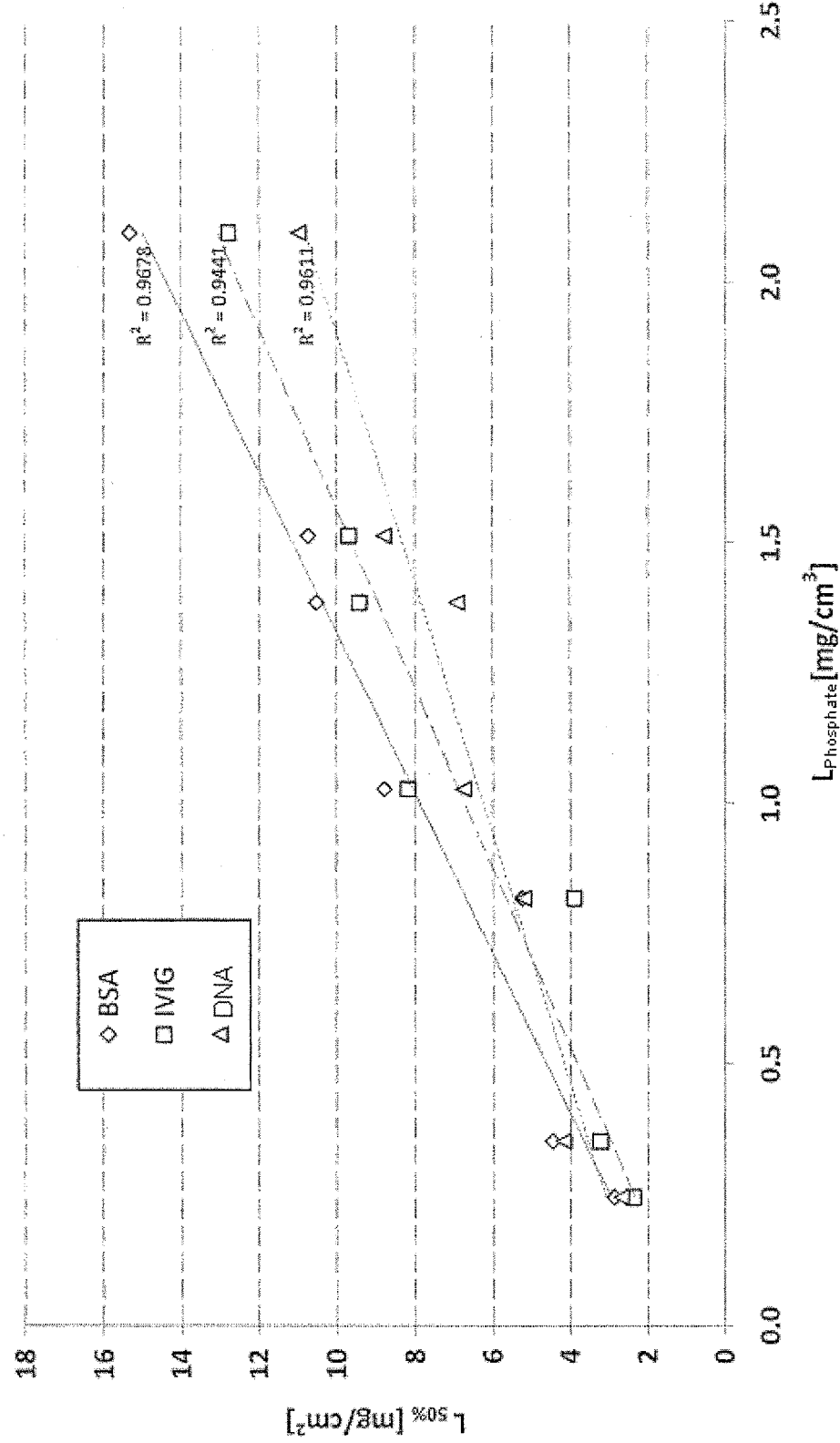
FIG. 6 shows the correlation between the phosphate loading number $L_{Phosphate}$ and the dynamic binding capacities for BSA, DNA and IVIG (DBT 50%) for various adsorptive depth filter sheet systems comprising inorganic layered double hydroxide.

The absorbances of the filtrate is recorded in fractions in a computer-controlled photometer at a wavelength of a) 280 nm for BSA, b) 260 nm for DNA and c) 280 nm for IVIG, and the concentration of the particular test substance is determined using standard series. Evaluation is carried out by dividing the absorbance of the filtrate by the absorbance of the test solution used and plotting this value against the filtration volume. The breakthrough curves are evaluated by determining the 50% dynamic breakthrough (DBT) and the cumulative binding over the entire course of filtration. The results are shown in Table 3 and in FIG. 6.

TABLE 3

Results of the dynamic binding capacities of BSA, DNA and IVIG and of the phosphate-binding capacity for various adsorptive depth filter sheets comprising inorganic layered double hydroxide

| Filter | Thickness [cm] | $V_D$ [ml] | $L_{Phosphate}$ [mg/cm$^3$] | DBT BSA 0.5* [mg/cm$^2$] | DBT DNA 0.5* [mg/cm$^2$] | DBT IVIG 0.5* [mg/cm$^2$] |
|---|---|---|---|---|---|---|
| No. 1 (39% hydrotalcite type A) | 0.37 | 69.09 | 1.028 | 8.79 | 6.74 | 8.17 |
| No. 2 (46% hydrotalcite type A) | 0.39 | 105.93 | 1.513 | 10.72 | 8.80 | 9.67 |
| No. 3 (64% hydrotalcite type A) | 0.33 | 140.02 | 2.096 | 15.33 | 10.96 | 12.77 |
| No. 4 (64% hydrotalcite type C) | 0.29 | 76.79 | 1.385 | 10.50 | 6.92 | 9.42 |
| No. 5 (58% hydrotalcite type B) | 0.35 | 51.23 | 0.818 | 5.23 | 5.19 | 3.89 |
| No. 6 (50.9% hydrotalcite type B) | 0.41 | 26.10 | 0.351 | 4.45 | 4.16 | 3.22 |
| No. 7 (46.2% hydrotalcite type B) | 0.38 | 16.72 | 0.244 | 2.86 | 2.68 | 2.37 |

*Corresponds to the loading at 50% dynamic breakthrough of the starting concentration It is apparent that there is a linear correlation between the phosphate loading number $L_{Phosphate}$ (as calculated in Example 2) and the dynamic binding capacities of BSA, DNA and IVIG, which allows a precise and reliable prediction of the binding capacities for said biomolecules depending on the experimentally determined phosphate loading number.

Example 7 —Restoration of Binding Capacity after Prior Phosphate Loading for the Purpose of Checking Adsorption Capacity To restore (reload) binding capacity after prior application of phosphate during the integrity test (as per Example 2), a filter punch-out having a diameter of 47 mm and an effective filter area of 13.2 cm² is inserted into a stainless steel filtration housing (from Sartorius Stedim Biotech GmbH) while still wetted or left in said housing directly after the prior phosphate test. Binding capacity is restored by rinsing with 50 ml of a 500 mmol/l potassium carbonate solution and subsequent rinsing with 100 ml of TBS (as per Example 1) at a flow rate of 5 ml/min. After this treatment, the BSA binding capacity of the depth filter treated with the phosphate test is 91% of the BSA binding capacity of an untreated depth filter punch-out (see Table 4).

TABLE 4

Restoration of the binding capacity of adsorptive depth filter sheet systems comprising inorganic layered double hydroxide. Influence of concentration and rinse volume of the carbonate-containing rinse solution on the restoration of binding capacity (reload).

| Concentration/ rinse volume | DBT BSA 0.5* [mg/cm³] | DBT BSA 0.03** [mg/cm³] | DBT 0.5 BSA % loading after regeneration |
|---|---|---|---|
| Reference 0 ml | 11.257 | 7.500 | 1.00 |
| TBS rinse 50 ml | 6.698 | 4.387 | 0.60 |
| Carbonate/TBS rinse 50 ml 50 mmol/l | 7.309 | 4.816 | 0.65 |
| Carbonate rinse 50 ml 50 mmol/l | 8.978 | 6.385 | 0.80 |
| Carbonate rinse 50 ml 500 mmol/l | 10.231 | 7.266 | 0.91 |
| Carbonate rinse 2 × 25 ml 500 mmol/l | 10.761 | 7.185 | 0.96 |

*DBT 0.5: Loading of the filter at 50% dynamic breakthrough of the starting concentration
**DBT 0.03: Loading of the filter at 3% dynamic breakthrough of the starting concentration Table 4 shows that rinsing with a carbonate-free buffer solution leads to a 60% regeneration of BSA binding capacity.

Rinsing with carbonate-containing buffer solution and subsequent rinsing with carbonate-free buffer solution improves the regeneration of BSA binding capacity to 65%. In the case of use of nonbuffered carbonate solution, the regeneration of BSA binding capacity rises from 80% at 50 mmol/l to 91% at 500 mmol/l. According to the last row in Table 4, an improvement in the regeneration of BSA binding capacity to a level of 96% is reached by applying two portions comprising in each case 25 ml of nonbuffered carbonate solution (500 mmol/l) to the depth filter, with an exposure time of 30 minutes between the two portions. The method according to the invention thus allows a simple, cost-effective and almost quantitative regeneration of the depth filter for the subsequent intended use to adsorb biomolecules.

Example 8 —Restoration of Binding Capacity after Prior Phosphate Loading for the Purpose of Checking Adsorption Capacity To restore (reload) binding capacity after prior application of phosphate ions during the integrity test (as per Example 2), a filter punch-out having a diameter of 47 mm and an effective filter area of 13.2 cm² is inserted into a stainless steel filtration housing (from Sartorius Stedim Biotech GmbH) while still wetted or left in said housing directly after the prior phosphate test. Reloading is achieved by rinsing with 2×25 ml of a 500 mmol/l potassium carbonate solution at a flow rate of 5 ml/min, with the flow rate being set to 0 ml/min for the period of 30 min between the first 25 ml rinse volume and the second 25 ml rinse volume and rinsing subsequently being carried out with 100 ml of TBS (as per Example 1) at a flow rate of 5 ml/min. After this treatment, the BSA binding capacity of the depth filter treated with the phosphate test is 96% of the BSA binding capacity of an untreated depth filter punch-out (see Table 4).

Figure 7:
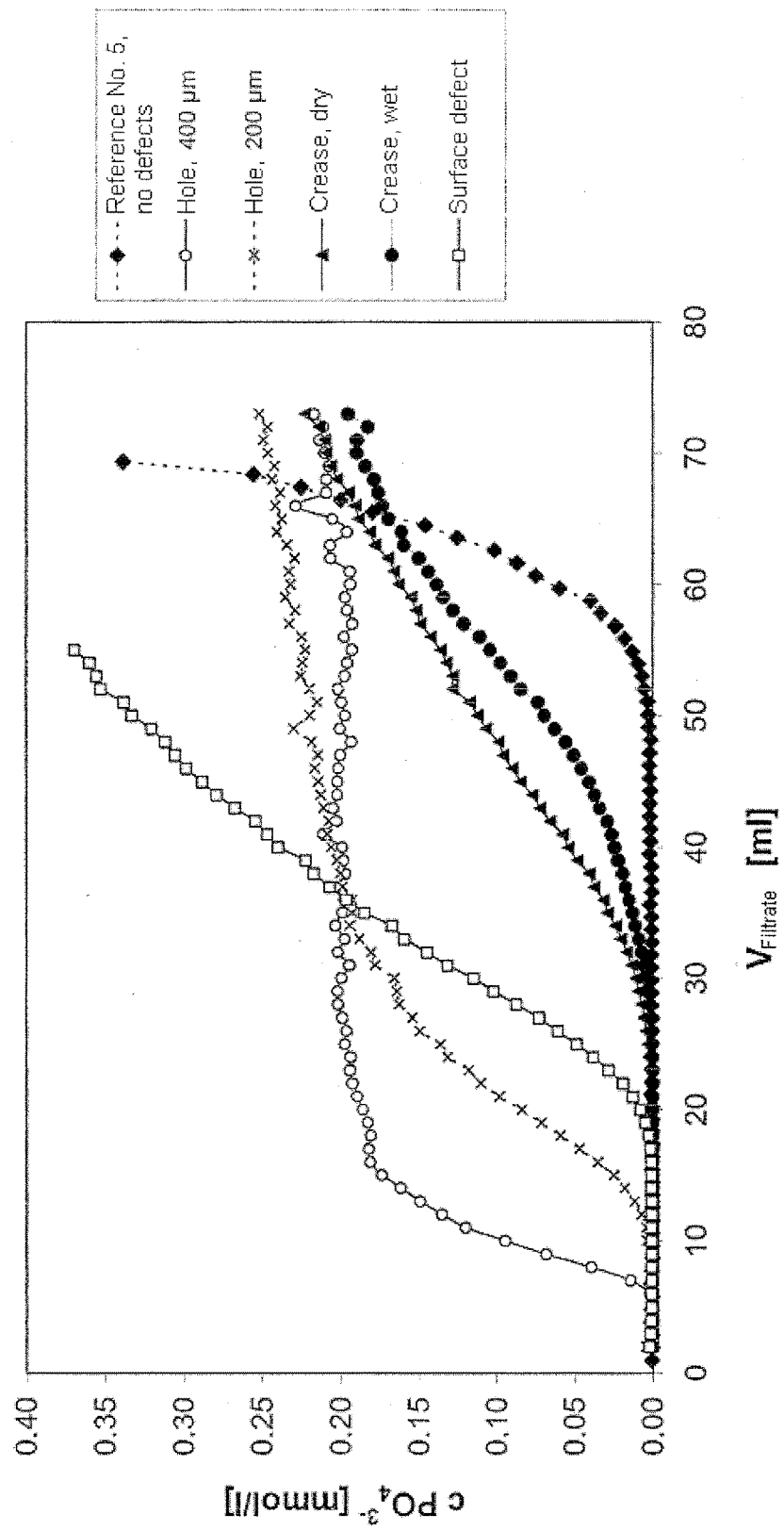
FIG. 7 shows the phosphate breakthrough curves on the adsorptive depth filter sheet system comprising inorganic layered double hydroxide No. 4 during the application of phosphate ions at a concentration of 1 mmol/l as per Example 2 following the introduction of various defects.

Example 9 —Phosphate Breakthrough Curves on Adsorptive Depth Filter Sheet Systems Comprising Inorganic Layered Double Hydroxide During the Application of Phosphate Ions Following Introduction of Artificial Defects In the dry state, a punch-out of an adsorptive depth filter sheet system comprising inorganic layered double hydroxide having the diameter of 47 mm and an effective filter area of 13.2 cm² is provided with a single hole in the center of the filter punch-out by means of a stainless steel needle. This involved using needles having a diameter of 200 µm or 400 µm. The rest of the procedure to determine the phosphate breakthrough is as described in Example 2. The breakthrough curve is shown in FIG. 7.

Example 10 —Phosphate Breakthrough Curves on Adsorptive Depth Filter Sheet Systems Comprising Inorganic Layered Double Hydroxide During the Application of Phosphate Ions Following Introduction of Artificial Defects A punch-out of an adsorptive depth filter sheet system comprising inorganic layered double hydroxide having the diameter of 47 mm and an effective filter area of 13.2 cm² is wetted with 10 ml of RO water and provided with a single hole in the center of the filter punch-out by means of a stainless steel needle having a diameter of 400 µm. The rest of the procedure to determine the phosphate breakthrough is as described in Example 2. The breakthrough curve is shown in FIG. 7.

Example 11 —Phosphate Breakthrough Curves on Adsorptive Depth Filter Sheet Systems Comprising Inorganic Layered Double Hydroxide During the Application of Phosphate Ions Following Introduction of Artificial Defects In the dry state, a punch-out of an adsorptive depth filter sheet system comprising inorganic layered double hydroxide having the diameter of 47 mm and an effective filter area of 13.2 cm² is provided with a crease, breaking the surfaces of the depth filter sheet. The rest of the procedure to determine the phosphate breakthrough is as described in Example 2. The breakthrough curve is shown in FIG. 7.

Example 12 —Phosphate Breakthrough Curves on Adsorptive Depth Filter Sheet Systems Comprising Inorganic Layered Double Hydroxide During the Application of Phosphate Ions Following Introduction of Artificial Defects In the dry state, the surface of a punch-out of an adsorptive depth filter sheet system comprising inorganic layered double hydroxide having the diameter of 47 mm, a thickness of 0.37 mm and an effective filter area of 13.2 cm$^2$ is destroyed on the upstream side. To this end, tweezers were used to remove from the depth filter material in the dry state approximately the top half of the material across the entire inflow area. This avoided a complete physical breakthrough through the entire thickness of the depth filter sheet. The rest of the procedure to determine the phosphate breakthrough is as described in Example 2. The breakthrough curve is shown in FIG. 7.

FIG. 7 illustrates that the high sensitivity of the method according to the invention makes it possible to detect very easily even small defects in the filter, because the position of the breakthrough point responds very sensitively to the presence of defects.

The invention claimed is:

1. A method for determining the integrity and functionality of depth filter sheets and depth filter sheet systems comprising inorganic layered double hydroxides, comprising the steps of
    loading the depth filter sheet comprising inorganic layered double hydroxide with an adsorbate, comprising inorganic anions, under conditions under which the adsorbate is completely retrained by the adsorptive depth filter sheet until the breakthrough volume is reached,
    detecting the broken-through adsorbate by means of a secondary reaction, the limit of detection of a detected species, D, is p[D]≥4, wherein p[D] is the negative common logarithm of the concentration of species [D], and
    comparing the breakthrough characteristics with those of an adsorptive depth filter sheet of known integrity,
    wherein the depth filter sheet comprises, in addition to cellulose fibers and the inorganic layered double hydroxide, no further pulverulent adsorbent.

2. The method as claimed in claim 1, wherein the inorganic anions encompass phosphate ions from the group of oxygen acids of phosphorus.

3. The method as claimed in claim 2, wherein the secondary reaction encompasses a complex formation with a color reaction with formation of a phosphomolybedenum blue complex.

4. The method as claimed in claim 1, wherein the loading with the adsorbate is reversible.

5. The method as claimed in claim 1, further comprising the step of rinsing the depth filter sheet comprising inorganic layered double hydroxide with a carbonate-containing rinse solution, resulting in the depth filter sheet regaining at least 90% of its original binding capacity for a subsequent intended use.

6. The method as claimed in claim 1, wherein the proportion by weight of the inorganic layered double hydroxide in the depth filter sheet is 20% or more.

7. The method as claimed in claim 1, wherein the inorganic layered double hydroxide comprises hydrotalcite.

8. The method as claimed in claim 1, wherein the breakthrough of the inorganic ions correlates with the retention capacity with respect to biomolecules.

9. The method as claimed in claim 8, wherein the biomolecules are selected from the group of serum albumins, nucleic acids and immunoglobulins or combinations thereof.

* * * * *